United States Patent [19]

Ziemann

[11] Patent Number: 4,973,334
[45] Date of Patent: Nov. 27, 1990

[54] DEVICE FOR EJECTING OR TAKING IN LIQUID OR PASTE-LIKE MEDIA

[75] Inventor: Edeltraud Ziemann, Inning am Holz, Fed. Rep. of Germany

[73] Assignee: Allo Pro Ag, Switzerland

[21] Appl. No.: 366,657

[22] Filed: Jun. 14, 1989

Related U.S. Application Data

[63] Continuation of Ser. No. 116,450, Nov. 3, 1987, abandoned.

[30] Foreign Application Priority Data

Jan. 16, 1987 [DE] Fed. Rep. of Germany ....... 3701190

[51] Int. Cl.$^5$ .................................................. A61F 5/04
[52] U.S. Cl. ......................................... 606/92; 606/93; 606/94
[58] Field of Search .......................... 192/0.02 R, 56 R; 128/2 VP, 92 VQ, 303 R, DIG. 1; 74/413, 44 R; 408/10, 11, 20, 21, 22, 24, 129; 606/92, 93, 94; 222/249

[56] References Cited

U.S. PATENT DOCUMENTS

| | | | |
|---|---|---|---|
| 2,299,268 | 10/1942 | Fisher | 128/303 R |
| 3,811,442 | 5/1974 | Maroth | 128/DIG. 1 |
| 3,812,843 | 5/1974 | Wootten et al. | 128/DIG. 1 |
| 4,157,716 | 6/1979 | Rüegg | 128/DIG. 1 |
| 4,595,006 | 6/1986 | Burke et al. | 128/92 VQ |
| 4,711,609 | 12/1987 | Seefluth | 408/68 |

FOREIGN PATENT DOCUMENTS 3425566 1/1986 Fed. Rep. of Germany ... 128/92 V

Primary Examiner—Robert A. Hafer
Assistant Examiner—Charles H. Sam
Attorney, Agent, or Firm—Andrus, Sceales, Starke & Sawall

[57] ABSTRACT

For the application of bone cement, the cement must be ejected with maximum uniformity. The proposed device comprises a cylinder (10) including a distal ejection nozzle (11), said cylinder with its proximal end (12) being adapted for mounting on a displacing unit (20) for displacing a piston (13). The displacing unit (20) comprises gear means (21, 22) for converting the rotary movement of a driving journal (23) into the linear displacing movement of a driven plunger (14). The piston (13) is adapted to be connected with the driven plunger (14). In the vicinity of the driving journal (23) the displacing unit (20) comprises adapter means (30) for detachable assembly with a pneumatic drilling machine (40).

11 Claims, 1 Drawing Sheet

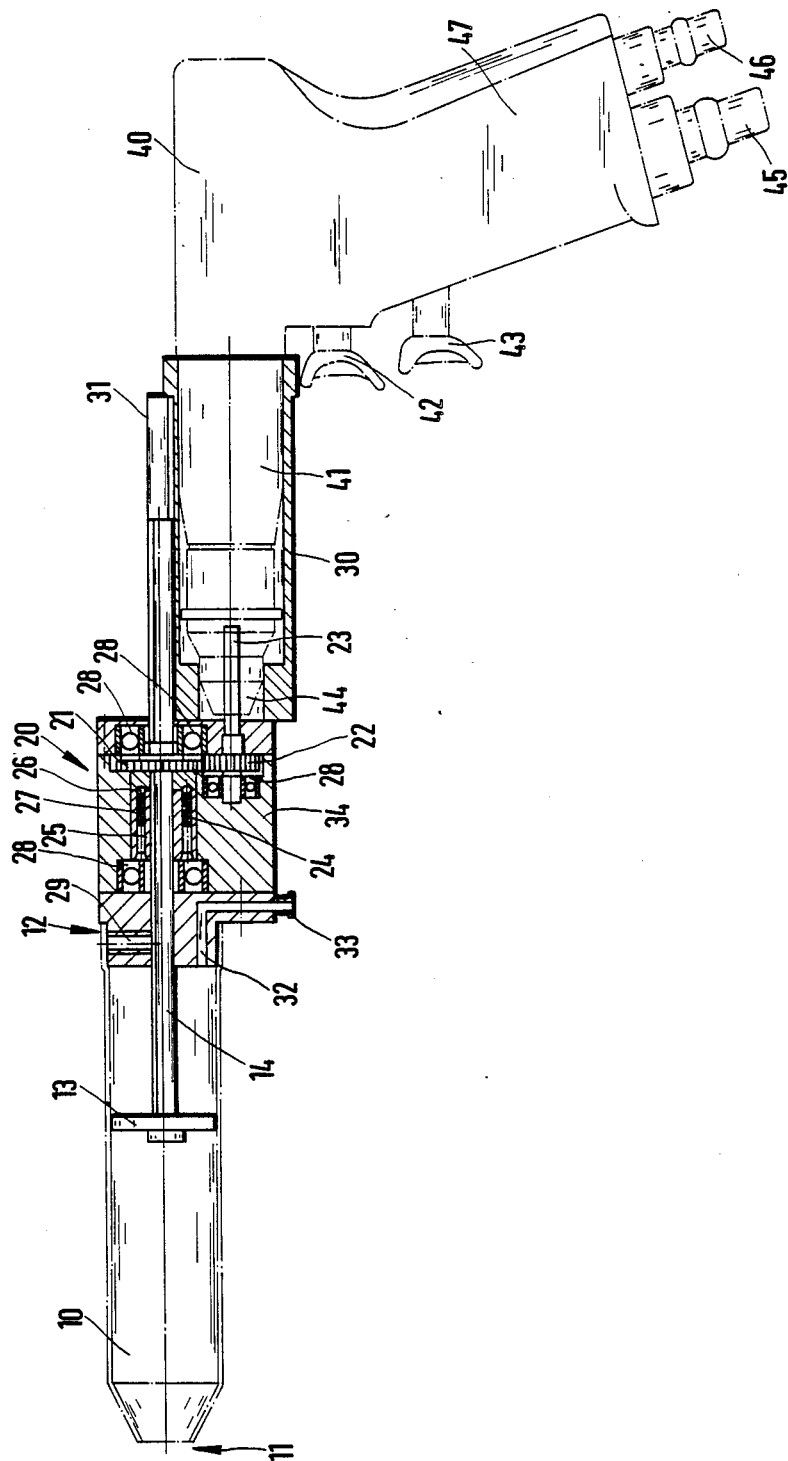

DEVICE FOR EJECTING OR TAKING IN LIQUID OR PASTE-LIKE MEDIA

This is a continuation of application Ser. No. 07/116,450, filed Nov. 3, 1987 now abandoned.

BACKGROUND OF THE INVENTION

The present invention is directed to a device for ejecting or taking in liquid or paste-like media as specified in the preamble of patent claim 1.

In joint surgery, where endoprostheses must be firmly joined to the bone, a bed is initially cut from the bone in which subsequently the prosthesis is secured by means of bone cement. In order to achieve a perfect bond between the bone cement and the bone, the bed must be flushed so as to be substantially completely free from bone residue (caused during cutting) or the like. Exhausting of the flushing liquid is a relatively critical operation and must be performed only at a relatively low negative pressure which should also be controllable.

Furthermore, the bone cement, which is a high-viscosity "two-component synthetic resin", must be introduced into the prepared bed and this operation also must be controllable.

CH-PS 546,075 discloses a manually operated device for introducing bone cement, which is configured like a commercially available hypodermic needle. But the operation of this device requires considerable energy.

In addition to that, devices are available which are designed similarly to the operating means for plastic cartridges and permit high-energy step-wise advance of a control piston via a lever provided on a pistol grip. But these devices are basically unsuited for ensuring continuous filling of the bone cement, thus resulting in non-uniform and therefore imperfect filling with bone cement.

The journal "med.-Orthop.-Techn." 6/86; p. 203, discloses a pneumatic device of the initially specified kind, in which the piston for ejecting the bone cement is actuated by compressed air directly through a piston-and-cylinder system so that bone cement can be ejected continuously and without undue effort by the operator. It is an essential problem of this device that the bone cement ejection rate (volume per unit of time) must be performed through a correspondingly sensitive actuation of valves which control the air supply to the actuating cylinder. It has been found that the operator must work with extreme care so that bone cement is uniformly ejected in the desired manner in response to its respective current viscosity (which varies with time). As the atmosphere in an operating room is well known to be frequently quite hectic, "operating errors" with fatal consequences may easily happen.

On the basis of the above-specified prior art it is the object of the present invention to improve a device of the initially specified kind in such a way that uniform ejection with little energy expenditure becomes possible.

SUMMARY OF THE INVENTION

The above-specified object is solved by the features set out in the characterizing portion of patent claim 1. Preferred embodiments of the invention will be apparent from the subclaims.

Due to the fact that the rotary motion of a pneumatic drilling machine is converted into a linear displacing motion it becomes possible to ensure a constant ejection rate substantially independently of the required ejection pressure in the cylinder. On the other hand, the same device may be used for exhausting by "left-handed operation" of the pneumatic drilling machine, whereby the piston is retracted within the cylinder.

A further essential advantage of the present invention resides in that already existing pneumatic drilling machines, which have been adapted to the special conditions prevailing in the operating room, can easily be refitted so that both the exhaustion of flushing liquid and the ejection of bone cement becomes possible in the desired precise way.

Of course, the device according to the present invention is not only suited for ejecting bone cement but is also useful for other compositions which must be applied with maximum uniformity, this being the case, for instance, with contrast media.

It is preferred that limiting means is provided for limiting the maximum power acting on the driven plunger and thus on the ejecting piston. On the one hand, this offers increased safety in respect of the application of excessive ejection pressures, and on the other hand the bone cement may thereby be pre-compressed at a defined pressure whereby an improved polymerizing reaction can be obtained. For such a pre-compression the ejection nozzle is initially closed and the piston urged into the cylinder until the limiting means prevents any further pressure increase. When the gear means comprises, as in a preferred embodiment of the present invention, a threaded sleeve which is rotated by the drilling machine and advances the driven plunger via a corresponding complementary external screw thread, it is possible after said maximum pressure for pre-compression has been reached to maintain the pressure constant by simply shutting the drilling machine off, because the gear is of the "self-locking type". Prior to the opening of the ejection nozzle the drilling machine is then briefly operated left-handedly so that the pressure is decreased to a sufficient extent.

Preferably, the piston is sealed relative to the cylinder by a sealing laminate so that any air stirred into the composition as well as any gases formed during the reaction may escape while the high-viscosity bone cement cannot overcome the seal. The "degasifying effect" is especially advantageous when a negative pressure is developed rearwardly of the piston. To this end a preferred embodiment of the present invention is provided with an exhaust port including a corresponding exhaust fitting in the vicinity of the driven plunger.

BRIEF DESCRIPTION OF THE DRAWING

The drawing is a sectional view of a displacing unit for paste-like material.

DESCRIPTION OF PREFERRED EMBODIMENTS

An example of a preferred embodiment of the present invention will be described in detail below with reference to the drawing, which is a partial longitudinal sectional view of the instant device.

As will be apparent from the drawing, the device of the present invention comprises a displacing unit 20 adapted to be mounted on a commercially available pneumatic drilling machine 40. To this end the displacing unit 20 includes adapter means 30 comprising a sleeve with distal chucking means for interlocking with the neck 41 of the drilling machine 40. After tightening of the chucking means (not illustrated) the adapter means 30 will be securely joined to the drilling machine 40.

The adapter means 30 is fixedly connected with a transmission mission casing 34. Within the transmission casing 34 a gear 22 is supported (ball bearing 28) which is mounted on a driving journal 23 projecting from the casing 34. The adapter means 30 extends in coaxial relationship about the driving journal 23 which preferably has an angular peripheral surface. The peripheral surface of the driving journal 23 is configured such that the driving journal 23 is in interlocking engagement inside the clamping chuck 44 of the drilling machine 40 when the clamping chuck 44 is sufficiently opened.

Moreover the transmission casing 34 has a threaded sleeve 25 mounted therein (ball bearing 28) for rotation but axially non-displaceable in parallel but laterally offset relationship with the driving journal 23, said threaded sleeve being operatively connected to a further gear 21, which is in meshing engagement with the first gear 22, via a spring-loaded ball-type clutch comprising springs 27 and balls 26. The assembly comprising threaded sleeve 25, friction clutch 24 and gear 21 is supported on either side to ensure sufficient stability. Springs 27 provide a force adjusting control.

In coaxial relationship with the sleeve 25 the casing 34 is formed with a bore having a larger diameter than the internal threads of the sleeve 25. This bore within the casing 34 is adapted to accommodate a driven plunger 14 provided with an external screw thread 34a which is complementary with the internal screw thread 34b of the threaded sleeve 25. Thus, in the fully inserted condition the threaded sleeve 25 is mounted on the external screw thread of the driven plunger 14.

The driven plunger 14 is provided with a groove which extends along the length of the plunger and in which (in the mounted state) a pin 29 engages which is inserted in the casing 34 or the front portion thereof normal to the axis of the driven plunger 14. In this way the driven plunger 14 is longitudinally movably but non-rotatably retained within the casing 34.

At the end of the casing 34 which is remote from the drilling machine 40, adapter means (bayonet clutch) is provided for securing the distal end of a cylinder 10 to the casing 34. Such cylinders 10 are commercially available disposable parts and do not require further explanation. The front end of the cylinder is provided with an ejection nozzle 11.

The end of the driven plunger 14 has a piston 13 mounted thereon which is provided with a continuous sealing laminate (not illustrated).

The end of the casing 34 which is remote from the drilling machine 40 is furthermore provided with a bore 32 which extends to an exhaust fitting 33 and to which a tube may be coupled for connection to a vacuum pump. The space behind the piston 13 can be evacuated via said fitting, so that any air inclusions and reaction gases possibly present in the mixture may be exhausted.

On top of the adapter means 30 a protective cap 31 is provided in which the end of the driven plunger 14 opposite the piston 13 may run so that the end of the driven plunger 14 will always be protected even with the piston 13 fully retracted.

The drilling machine 40 is provided with two valves through the control buttons 42, 43 of which the drilling machine 40 can be operated with right-handed or left-handed rotation. The control buttons 42 and 43 protrude from a "pistol grip" 47 of the drilling machine 40.

The end face of the pistol grip 47 has a compressed-air fitting 45 and an exhaust air fitting 46 protruding therefrom; through the latter, the normally non-sterile compressed-air can be exhausted from the operating room.

In another, preferred embodiment of the invention, which is not illustrated, a worm gear is provided instead of the gear 22 and is connected via a friction clutch to the driving journal 23. The driven plunger 14 of this preferred embodiment is not provided with a continuous screw thread but merely has teeth provided thereon for meshing engagement with the worm gear.

It is one of the essential advantages of the invention that an already existing pneumatic drilling machine 40, which is adapted to the conditions prevailing in an operating room, can easily be used for the application of bone cement or for exhausting media of any kind, wherein the application of bone cement can be very well metered. The entire device can readily be manufactured so as to be sterilizable by steam, which is normally not the case with electrically powered devices. Moreover, the friction clutch provides a safety feature against excessive ejection pressures, and furthermore the bone cement can be pre-compressed in the desired and, above all, reproducible way.

The above-described details are claimed as being essential to the invention both individually and in combination to the extent to which they are novel.

We claim:

1. A device for transferring of extrudable material in the form of liquid and paste-like substance during medical procedures including joint surgery and for ejecting or taking in liquid and paste-like substances in medical procedures, especially in the field of joint surgery, comprising a cylinder (10) having a distal transfer nozzle (11), cylinder, a displacing unit (20) for displacing said piston (13), said displacing unit (20) having a supporting body and a rotating driving journal (23) and gear means (21, 22) within said body for converting the rotary motion of said driving journal (23) to a linear displacing motion, a driven plunger (14) connected to said gear means and connected to said piston (13), and a drive connecting means (30) secured to said body, said drive connecting means including a detachable mounting means for receiving a rotary pneumatic drilling machine (40) having a rotary driven output complementing and releasably coupled to said driving journal.

2. The device of claim 1, wherein said gear means (21, 22) includes a power limiting means (24) for limiting the power transmitted to the journal and said driven plunger (14).

3. The device of claim 2, wherein said limiting means (24) is a torque-limiting friction clutch.

4. The devices of claim 3, wherein said clutch includes a spring-loaded ball-type clutch (26-27).

5. The device of claim 2, wherein said limiting means (24) includes a force adjusting unit to adjust said torque.

6. The device of claim 1 having a transmission casing mounted to the end of said cylinder, said gear means includes a threaded sleeve (25) mounted for rotation and axially immovable in said transmission casing (34), said driven plunger (14) having a corresponding external screw thread and threaded into said sleeve, and means holding said plunger against rotation and longitudinally movable within the transmission casing (34).

7. The device of claim 5, wherein said gear means including a coaxially mounted gear to operatively connected to said threaded sleeve (25) and a gear (22) mounted on said driving journal (23) and in meshing engagement with gear 21.

8. The device of claim 6 having a power limiting means connected between said threaded sleeve (25) and gear (21).

9. The device of claim 1, wherein said displacing unit (20) includes means detachably secured to the proximal end of said cylinder (10) for separating said cylinder.

10. The device of claim 1, wherein said displacing unit (20) includes means (32, 33) for exhausting gases from the cylinder (10) rearwardly of said piston (13).

11. The device of claim 1, including a sealing laminate between the circumference of said piston (13) to said cylinder (10) to slidably seal the space therebetween.

* * * * *

UNITED STATES PATENT AND TRADEMARK OFFICE
CERTIFICATE OF CORRECTION

PATENT NO. : 4,973,334
DATED : November 27, 1990
INVENTOR(S) : EDELTRAUD ZIEMAN It is certified that error appears in the above-identified patent and that said Letters Patent is hereby corrected as shown below:

Claim 1, col. 4, line 35, after "(11)" insert --- having proximal end (12), a piston (13) located in said---; Claim 7, col. 4, line 67, delete "5" and substitute therefor ---6---; Claim 7, col. 4, line 68, delete "including" and substitute therefor ---includes---; Claim 7, col. 4, line 68, delete "to" and substitute therefor ---(21)---; Claim 7, col. 5, line 3, delete "21" and substitute therefor ---(21)---; Claim 8, col. 5, line 4, delete "6" and substitute therefor ---7---.

Signed and Sealed this

Seventh Day of July, 1992

Attest:

DOUGLAS B. COMER

*Attesting Officer*  *Acting Commissioner of Patents and Trademarks*